United States Patent
Cordero Marcos et al.

(10) Patent No.: US 11,013,936 B2
(45) Date of Patent: May 25, 2021

(54) METHODS AND SYSTEMS FOR GENERATING DOSE ESTIMATION MODELS FOR RADIOTHERAPY TREATMENT PLANNING

(71) Applicant: Varian Medical Systems International AG, Palo Alto, CA (US)

(72) Inventors: María Cordero Marcos, Espoo (FI); Esa Kuusela, Espoo (FI); Hannu Laaksonen, Espoo (FI); Sami Petri Perttu, Helsinki (FI)

(73) Assignee: VARIAN MEDICAL SYSTEMS INTERNATIONAL AG

( * ) Notice: Subject to any disclaimer, the term of this patent is extended or adjusted under 35 U.S.C. 154(b) by 0 days.

(21) Appl. No.: 16/228,800

(22) Filed: Dec. 21, 2018

(65) Prior Publication Data

US 2020/0197726 A1 Jun. 25, 2020

(51) Int. Cl.
*A61N 5/10* (2006.01)

(52) U.S. Cl.
CPC ......... *A61N 5/1031* (2013.01); *A61N 5/1039* (2013.01); *A61N 5/1045* (2013.01); *A61N 2005/1032* (2013.01); *A61N 2005/1041* (2013.01)

(58) Field of Classification Search
None
See application file for complete search history.

(56) References Cited

U.S. PATENT DOCUMENTS

| 10,346,593 B2 | 7/2019 | Kuusela et al. |
| 2013/0085343 A1 | 4/2013 | Toimela et al. |
| 2015/0094519 A1 | 4/2015 | Kuusela et al. |

(Continued)

FOREIGN PATENT DOCUMENTS

| WO | 2018048507 A1 | 3/2018 |
| WO | 2018048575 A1 | 3/2018 |

OTHER PUBLICATIONS

Konstantinos Kamnitsas et al., "Efficient Multi-Scale 3D CNN with Fully Connected CRF for Accurate Brain Lesion Segmentation", Medical Image Analysis, Feb. 2017, pp. 61-78, vol. 36, Elsevier B.V.

(Continued)

*Primary Examiner* — Edwin C Gunberg
(74) *Attorney, Agent, or Firm* — Su IP Consulting

(57) ABSTRACT

Example methods and systems for generating dose estimation models for radiotherapy treatment planning are provided. One example method may comprise obtaining model configuration data that specifies multiple anatomical structures based on which dose estimation is performed by a dose estimation model. The method may also comprise obtaining training data that includes a first treatment plan associated with a first past patient and multiple second treatment plans associated with respective second past patients. The method may further comprise: in response to determination that automatic segmentation is required for the first treatment plan, performing automatic segmentation on image data associated with the first past patient to generate an improved first treatment plan, and generating the dose estimation model based on the improved first treatment plan and the multiple second treatment plans.

21 Claims, 7 Drawing Sheets

(56) References Cited

U.S. PATENT DOCUMENTS

| | | |
|---|---|---|
| 2015/0360056 A1 | 12/2015 | Xing et al. |
| 2016/0129282 A1 | 5/2016 | Yin et al. |
| 2016/0140300 A1* | 5/2016 | Purdie .................. G16H 20/10 |
| | | 705/2 |
| 2017/0177812 A1 | 6/2017 | Sjolund |
| 2018/0043182 A1 | 2/2018 | Wu et al. |
| 2018/0161596 A1 | 6/2018 | Kuusela et al. |
| 2018/0211725 A1 | 7/2018 | Purdie et al. |
| 2019/0220986 A1 | 7/2019 | Magro et al. |
| 2019/0232087 A1 | 8/2019 | Cordero Marcos et al. |
| 2019/0328348 A1 | 10/2019 | De Man et al. |
| 2019/0329072 A1 | 10/2019 | Magro et al. |
| 2019/0333623 A1 | 10/2019 | Hibbard |
| 2020/0104695 A1 | 4/2020 | Laaksonen et al. |
| 2020/0105394 A1 | 4/2020 | Laaksonen et al. |
| 2020/0105399 A1 | 4/2020 | Laaksonen et al. |

OTHER PUBLICATIONS

Olaf Ronneberger et al., "U-Net: Convolutional Networks for Biomedical Image Segmentation", Computer Science Department and Bioss Centre for Biological Signalling Studies, May 18, 2015.

The Extended European Search Report, European application No. 19199019.1, dated Feb. 19, 2020.

C Kontaxis et al., "Towards Fast Online Intrafraction Replanning for Free-breathing Stereotactic Body Radiation Therapy with the MR-linac", Physics in Medicine & Biology, 2017, pp. 7233-7248, vol. 62.

A. Hunt et al., "Adaptive Radiotherapy Enabled by MRI Guidance", Clinial Oncology, 2018, pp. 711-719, vol. 30.

International Search Report and Written Opinion of the International Searching Authority, International application No. PCT/EP2019/075682, dated Nov. 18, 2019.

* cited by examiner

METHODS AND SYSTEMS FOR GENERATING DOSE ESTIMATION MODELS FOR RADIOTHERAPY TREATMENT PLANNING

CROSS-REFERENCE TO RELATED APPLICATIONS

This application is related in subject matter to U.S. patent application Ser. No. 15/784,200 and Ser. No. 16/145,461. The U.S. patent applications, including any appendices or attachments thereof, are incorporated by reference herein in their entirety.

BACKGROUND

Unless otherwise indicated herein, the approaches described in this section are not prior art to the claims in this application and are not admitted to be prior art by inclusion in this section.

Radiotherapy is an important part of a treatment for reducing or eliminating unwanted tumors from patients. Unfortunately, applied radiation does not inherently discriminate between an unwanted tumor and any proximal healthy structures such as organs, etc. This necessitates careful administration to restrict the radiation to the tumor (i.e., target). Ideally, the goal is to deliver a lethal or curative radiation dose to the tumor, while maintaining an acceptable dose level in the proximal healthy structures. However, in practice, there are various challenges associated with radiotherapy treatment planning to deliver radiation doses that achieve this goal.

SUMMARY

According to examples of the present disclosure, methods and systems for generating dose estimation models for radiotherapy treatment planning. One example method may comprise obtaining model configuration data that specifies multiple anatomical structures based on which dose estimation is performed by a dose estimation model. The method may also comprise obtaining training data that includes a first treatment plan associated with a first past patient and multiple second treatment plans associated with respective second past patients. The method may further comprise: in response to determination that automatic segmentation is required for the first treatment plan, performing automatic segmentation on image data associated with the first past patient to generate an improved first treatment plan, and generating the dose estimation model based on the improved first treatment plan and the multiple second treatment plans.

DETAILED DESCRIPTION

The technical details set forth in the following description enable a person skilled in the art to implement one or more embodiments of the present disclosure.

Figure 1:
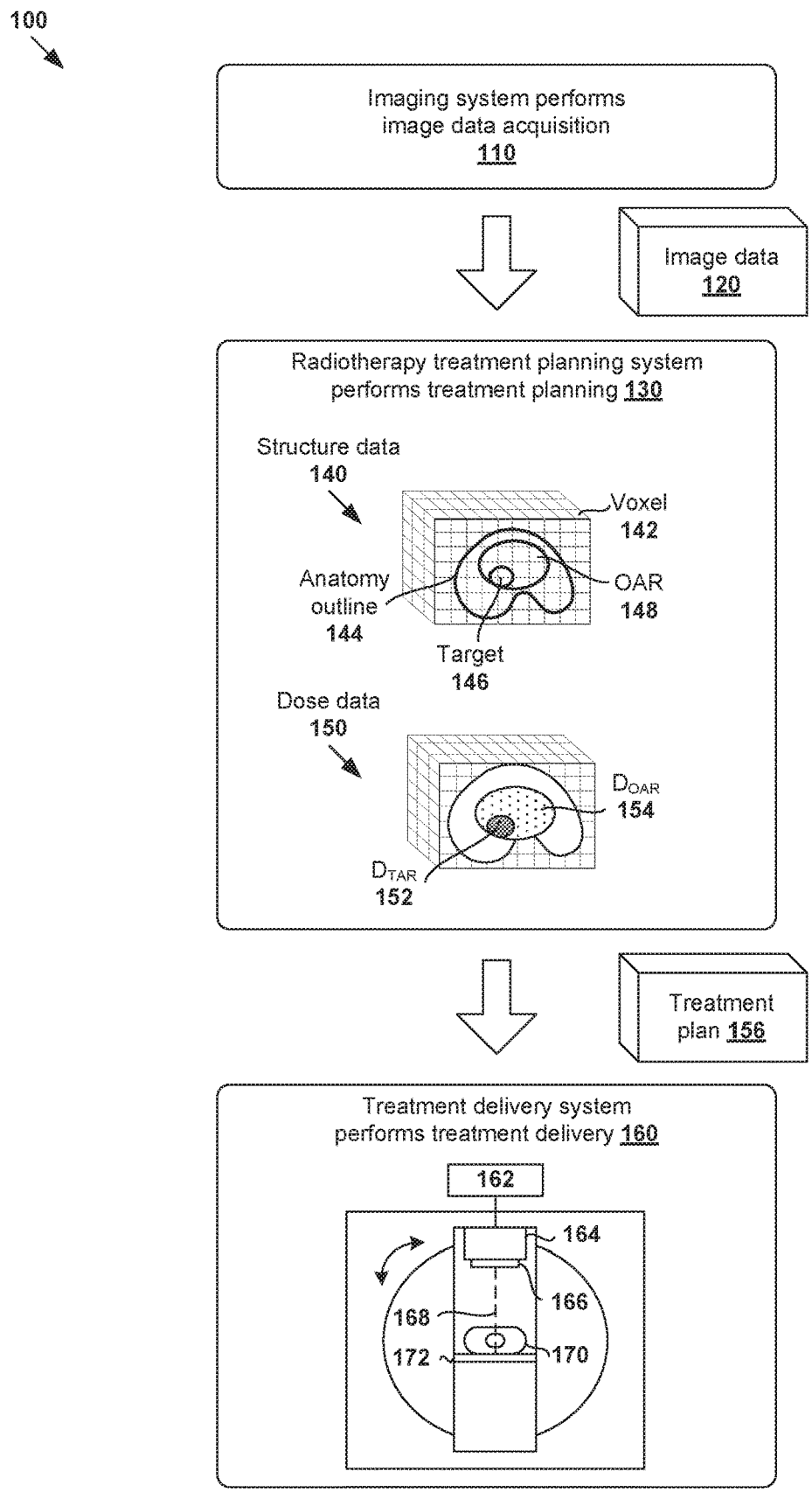
FIG. 1 is a schematic diagram illustrating an example process flow for radiotherapy treatment.

FIG. 1 is a schematic diagram illustrating example process flow 100 for radiotherapy treatment. Example process 100 may include one or more operations, functions, or actions illustrated by one or more blocks. The various blocks may be combined into fewer blocks, divided into additional blocks, and/or eliminated based upon the desired implementation. In the example in FIG. 1, radiotherapy treatment generally includes various stages, such as an imaging system performing image data acquisition for a patient (see 110); a radiotherapy treatment planning system (see 130) generating a suitable treatment plan (see 156) for the patient; and a treatment delivery system (see 160) delivering treatment according to the treatment plan.

In more detail, at 110 in FIG. 1, image data acquisition may be performed using an imaging system to capture image data 120 associated with a patient (particularly the patient's anatomy). Any suitable medical image modality or modalities may be used, such as computed tomography (CT), cone beam computed tomography (CBCT), positron emission tomography (PET), magnetic resonance imaging (MRI), single photon emission computed tomography (SPECT), any combination thereof, etc. For example, when CT or MRI is used, image data 120 may include a series of two-dimensional (2D) images or slices, each representing a cross-sectional view of the patient's anatomy, or may include volumetric or three-dimensional (3D) images of the patient, or may include a time series of 2D or 3D images of the patient (e.g., four-dimensional (4D) CT or 4D CBCT).

At 130 in FIG. 1, radiotherapy treatment planning may be performed during a planning phase to generate treatment plan 156 based on image data 120. Any suitable number of treatment planning tasks or steps may be performed, such as segmentation, dose prediction, projection data prediction, treatment plan generation, etc. For example, segmentation may be performed to generate structure data 140 identifying various segments or structures may from image data 120. In practice, a three-dimensional (3D) volume of the patient's anatomy may be reconstructed from image data 120. The 3D volume that will be subjected to radiation is known as a treatment or irradiated volume that may be divided into multiple smaller volume-pixels (voxels) 142. Each voxel 142 represents a 3D element associated with location (i, j, k) within the treatment volume. Structure data 140 may be include any suitable data relating to the contour, shape, size and location of patient's anatomy 144, target 146, organ-at-risk (OAR) 148, or any other structures of interest (e.g., tissues, bones). For example, using image segmentation, a line may be drawn around a section of an image and labelled as target 146 (e.g., tagged with label="prostate"). Everything inside the line would be deemed as target 146, while everything outside would not.

In another example, dose prediction may be performed to generate dose data 150 specifying radiation dose to be delivered to target 146 (denoted "$D_{TAR}$" at 152) and radiation dose for OAR 148 (denoted "$D_{OAR}$" at 154). In practice, target 146 may represent a malignant tumor (e.g., prostate tumor, etc.) requiring radiotherapy treatment, and OAR 148 a proximal healthy structure or non-target structure (e.g., rectum, bladder, etc.) that might be adversely affected by the treatment. Target 146 is also known as a planning target volume (PTV). Although an example is shown in FIG. 1, the treatment volume may include multiple targets 146 and OARs 148 with complex shapes and sizes. Further, although shown as having a regular shape (e.g., cube), voxel 142 may have any suitable shape (e.g., non-regular). Depending on the desired implementation, radiotherapy treatment planning at block 130 may be performed based on any additional and/or alternative data, such as prescription, disease staging, biologic or radiomic data, genetic data, assay data, biopsy data, past treatment or medical history, any combination thereof, etc.

Based on structure data 140 and dose data 150, treatment plan 156 may be generated include 2D fluence map data for a set of beam orientations or angles. Each fluence map specifies the intensity and shape (e.g., as determined by a multileaf collimator (MLC)) of a radiation beam emitted from a radiation source at a particular beam orientation and at a particular time. For example, in practice, intensity modulated radiotherapy treatment (IMRT) or any other treatment technique(s) may involve varying the shape and intensity of the radiation beam while at a constant gantry and couch angle. Alternatively or additionally, treatment plan 156 may include machine control point data (e.g., jaw and leaf positions), volumetric modulated arc therapy (VMAT) trajectory data for controlling a treatment delivery system, etc. In practice, block 130 may be performed based on goal doses prescribed by a clinician (e.g., oncologist, dosimetrist, planner, etc.), such as based on the clinician's experience, the type and extent of the tumor, patient geometry and condition, etc.

At 160 in FIG. 1, treatment delivery is performed during a treatment phase to deliver radiation to the patient according to treatment plan 156. For example, radiotherapy treatment delivery system 160 may include rotatable gantry 164 to which radiation source 166 is attached. During treatment delivery, gantry 164 is rotated around patient 170 supported on structure 172 (e.g., table) to emit radiation beam 168 at various beam orientations according to treatment plan 156. Controller 162 may be used to retrieve treatment plan 156 and control gantry 164, radiation source 166 and radiation beam 168 to deliver radiotherapy treatment according to treatment plan 156.

It should be understood that any suitable radiotherapy treatment delivery system(s) may be used, such as mechanic-arm-based systems, tomotherapy type systems, and internal radiotherapy delivery systems such as brachytherapy systems, radioembolization microspheres, and any combination thereof, etc. Additionally, examples of the present disclosure may be applicable to particle delivery systems (e.g., proton, carbon ion, etc.). Such systems may employ either a scattered particle beam that is then shaped by a device akin to an MLC, or a scanning beam of adjustable energy, spot size and dwell time.

An important aspect of radiotherapy treatment planning 130 is estimating the level of radiation dose to be applied to the patient. In practice, knowledge-based treatment planning may be used to estimate achievable doses for, inter alia, target 146 and OAR 148 based on existing clinical knowledge. This involves training a "dose estimation model" (also known as "dose prediction model") using a set of treatment plans (also known as "training data") previously devised for past patients. Ideally, the training data should be of high quality, and sufficiently similar to a treatment being planned for a new patient (e.g., similar treatment area, etc.). Once trained, the dose estimation model may be used to automatically generate treatment plan 156 for the new patient, or assist with the plan generation process.

Any suitable knowledge-based planning software may be used, such as RapidPlan™ (a trademark of Varian Medical Systems, Inc.), etc. Depending on the desired implementation, a dose estimation model may specify a relationship or rules to transform structure data or patient geometry data (i.e., known prior to optimization and called "independent data") into dose data (i.e., known after the optimization and called "dependent data"). When used with an optimization algorithm, estimates produced by the dose estimation model may be optimized according to optimization objectives set by a clinician to produce complete treatment plan 156. In other words, users (e.g., clinicians) may construct their own dose estimation models where the input for model training is a set of existing treatment plans, which are in turn analyzed automatically using a dedicated algorithm.

Conventionally, gathering enough treatment plans for the purpose of generating dose estimation model may be time and labor intensive. For example, to construct a dose estimation model for a set of anatomical structures of interest (e.g., OARs), a clinician should be careful to add enough treatment plans (i.e., training data) to properly model each of these anatomical structures. Otherwise, there will not be enough data to generate a dose estimation model that produces meaningful results to satisfy the desired treatment objectives. The process of adjusting and re-adjusting the training data is often manual, iterative and relies on the expertise of the clinician designing the dose estimation model.

Dose Estimation Model Generation Using Automatic Segmentation

According to examples of the present disclosure, radiotherapy treatment planning may be improved using automatic segmentation in combination with dose estimation model generation. Examples of the present disclosure may be implemented to improve the efficiency of radiotherapy treatment planning and possibly the treatment outcome, such as increasing the tumor control probability and/or reducing the likelihood of health complications or death due to radiation overdose in the healthy structures. For example, automatic segmentation would be of great benefit in speeding up the workflow of generating dose estimation models for radiotherapy treatment planning.

Figure 2:
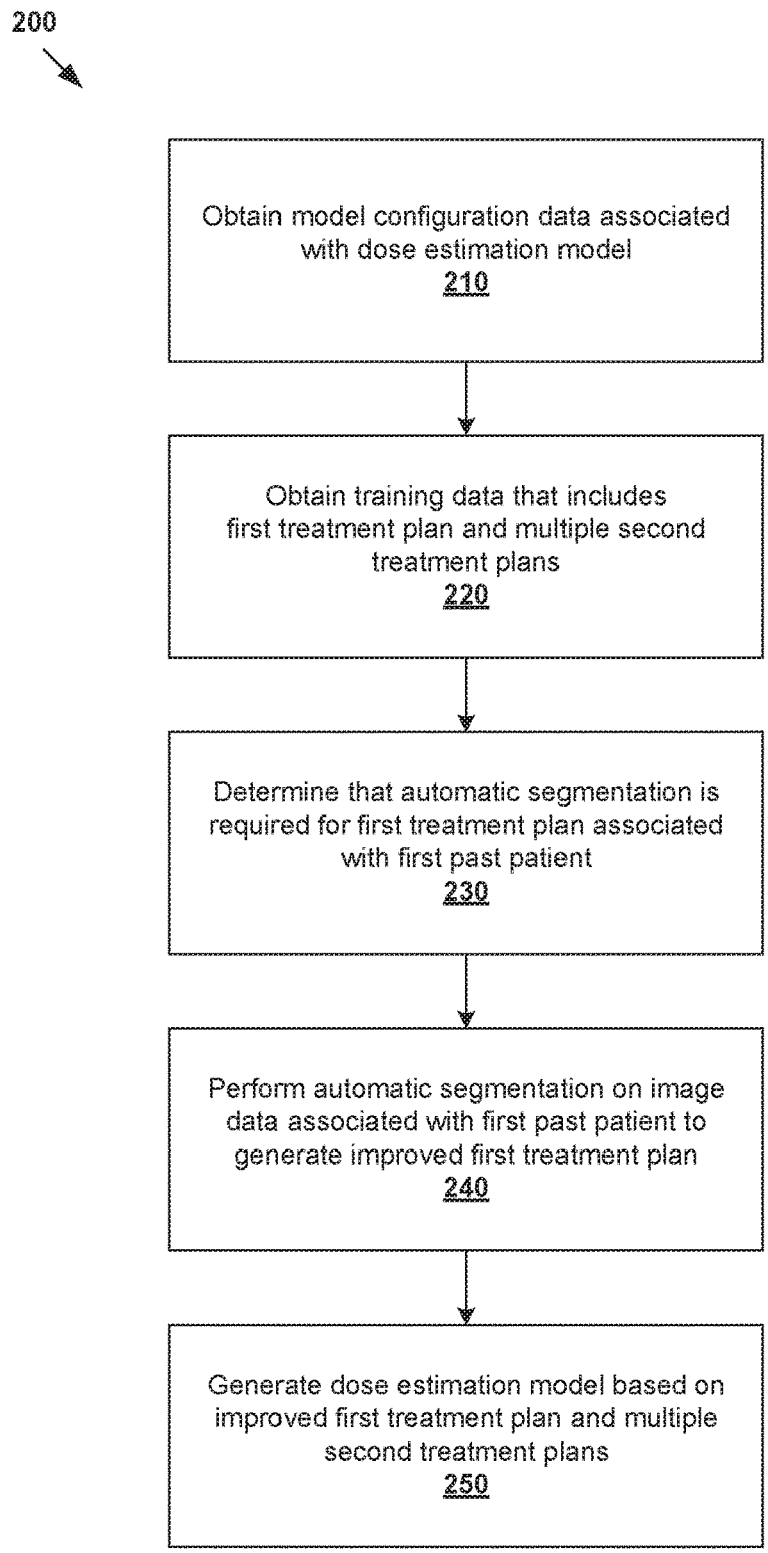
FIG. 2 is a flowchart of an example process for a computer system to generate a dose estimation model for radiotherapy treatment planning.

In more detail, FIG. 2 is a flowchart of example process 200 for a computer system to generate a dose estimation model for radiotherapy treatment planning. Example process 200 may include one or more operations, functions, or actions illustrated by one or more blocks, such as 210 to 250. The various blocks may be combined into fewer blocks, divided into additional blocks, and/or eliminated based upon the desired implementation. Example process 200 may be implemented using any suitable computer system(s), an example of which will be discussed using FIG. 7.

At 210 in FIG. 2, model configuration data associated with a dose estimation model may be obtained. The model configuration data may specify any suitable parameter(s) of the dose estimation model, including multiple anatomical structures based on which dose estimation is performed by the dose estimation model. In practice, the anatomical structures specified by the model configuration data may include target(s) 146, OAR(s) 148 and other proximal structure(s), etc. For example, in relation to prostate cancer treatment, a dose estimation model may perform dose estimation based on structure data associated with prostate (i.e., target), rectum, bladder, and femoral heads.

At 220 in FIG. 2, training data that includes a first treatment plan associated with a first past patient and multiple second treatment plans associated with respective multiple second past patients may be obtained. As used herein, the term "obtain" at blocks 210-220 may refer generally to retrieving the relevant data from any suitable storage (e.g., database storing the model configuration data, database of historical treatment plans) accessible by the computer system, receiving the data from another source via any suitable communication link, etc.

At 230 in FIG. 2, it is determined whether automatic segmentation is required for the first treatment plan. As will be discussed using FIG. 3, the determination at block 230 may involve determining whether the first treatment plan is an "outlier" based on at least one of the following: model configuration data, first structure data extracted from the first treatment plan, and first dose data extracted from the first treatment plan. Here, the term "outlier" may refer generally to a particular treatment plan from the training data that may adversely affect the optimality of the resulting dose estimation model.

Depending on the sub-optimal characteristic(s) detected, the first treatment plan may be a geometric outlier, dosimetric outlier, etc. Here, the term "sub-optimal characteristic" may refer to any suitable characteristic associated with the first treatment plan that may be reduced, or eliminated, to improve the optimality or quality of the first treatment plan (and subsequent dose estimation model). In one example, the first treatment plan to be a geometric outlier based on a sub-optimal characteristic associated with the first structure data, such as missing data due to missing contours of an organ, etc. In the case of prostate cancer treatment, for example, contours of femoral heads in the patient's prostate region might be missing. In another example, the first treatment plan to be a geometric outlier based on a sub-optimal characteristic associated with the first dose data, such as the first dose data not satisfying a threshold or following a dose distribution, etc.

At 240 in FIG. 2, in response to determination that automatic segmentation is required, automatic segmentation may be performed to generate an improved first treatment plan. Further, at 250 in FIG. 2, the dose estimation model may be generated based on the improved first treatment plan and the multiple second treatment plans. The improved first treatment plan includes structure data generated using automatic segmentation, the structure data identifying anatomical structure(s) specified by the model configuration data at block 210. Using automatic segmentation during radiotherapy treatment planning, the dose estimation model may be generated more efficiently. In practice, automatic segmentation may be used to achieve more consistent contours across the training data. A user (e.g., clinician) may apply automatic segmentation to a large set of training data to speed up the process of generating the dose estimation model.

Examples of the present disclosure should be contrasted against conventional approaches that rely on manual segmentation, which is slow, somewhat inconsistent and error prone. For example, it usually requires a team of highly skilled and trained oncologists and dosimetrists to manually delineate anatomical structures of interest by drawing contours or segmentations on image data. These structures are manually reviewed by a clinician, possibly requiring adjustment or re-drawing. In many cases, manual segmentation of critical organs can be the most time-consuming part of radiation treatment planning. Organs are contoured one-by-one, and if a new organ needs to be added, the new organ needs to be contoured in all the plans (or at least in enough plans for dose estimation modelling purposes).

Manual segmentation steps are often complicated by a lack of consensus among different physicians and/or clinical regions as to what constitutes "good" contours or segmentation. In practice, there might be a huge variation in the way structures or segments are drawn by different clinical experts. The variation may result in uncertainty in target volume size and shape, as well as the exact proximity, size and shape of OARs that should receive minimal radiation dose. Even for a particular expert, there might be variation in the way segments are drawn on different days. Examples of the present disclosure mitigate issue(s) associated with manual segmentation. In the following, various examples will be discussed using FIG. 3 to FIG. 7.

Model Configuration Data and Training Data

Figure 3:
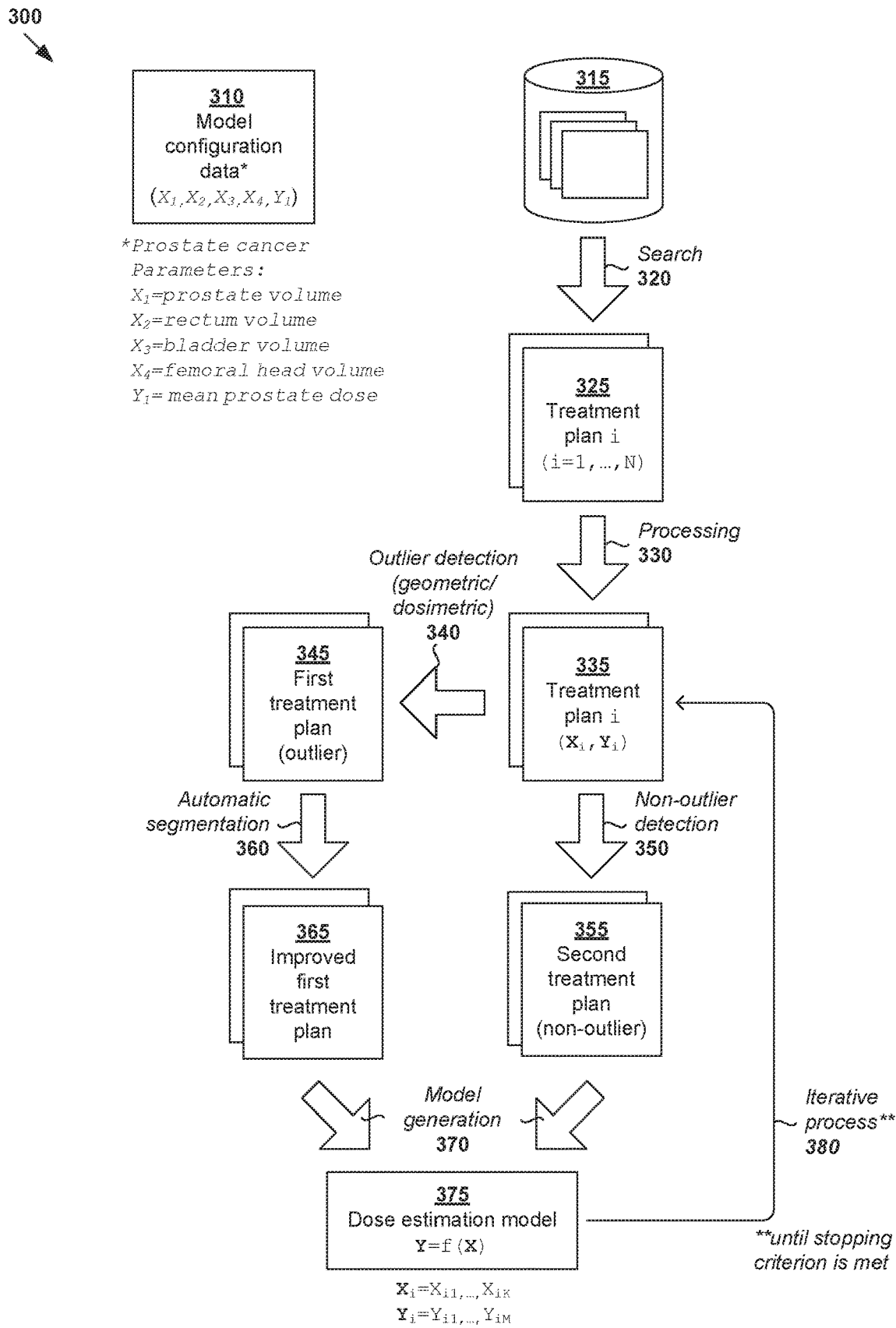
FIG. 3 is a schematic diagram illustrating an example detailed process for a computer system to generate a dose estimation model for radiotherapy treatment planning.

FIG. 3 is a schematic diagram illustrating example detailed process 300 for a computer system to generate a dose estimation model for radiotherapy treatment planning. Example process 300 may include one or more operations, functions, actions or data items illustrated by one or more blocks, such as 310 to 380. The various blocks may be combined into fewer blocks, divided into additional blocks, and/or eliminated based upon the desired implementation. Similar to the example in FIG. 2, example process 300 may be implemented using any suitable computer system, an example of which will be discussed using FIG. 7.

At 310 in FIG. 3 (related to 210 in FIG. 2), model configuration data associated with a dose estimation model is obtained. Here, the term "model configuration data" may refer generally to any suitable data defining feature(s) or parameter(s) of the dose estimation model for a particular treatment site. In the example in FIG. 3, model configuration data 310 may specify anatomical structures based on which dose estimation may be performed by a desired dose estimation model. In relation to prostate cancer, the dose estimation model may be generated to estimate dose data based on structure data associated with anatomical structures=(prostate, rectum, bladder, femoral head(s), etc.). The goal of dose estimation model training is to estimate a relationship between output=dose data, and input=structure data.

In practice, any additional and/or alternative radiotherapy treatment site(s) may be considered. For example, in relation to lung cancer, the dose estimation model may be configured to estimate dose data based on structure data associated with structures=(cancerous lung tissue, healthy lung tissue, esophagus, heart), etc. In relation to brain cancer, the dose estimation model may be configured to estimate dose data based on structure data associated with structures=(brain tumor, optic nerve, brain stem), etc. The structure data may identify any additional and/or alternative anatomical structure(s) in the treatment site. The model configuration data may be stored in a datastore in any suitable format (e.g., model binary).

Depending on the desired implementation, model configuration data 310 may be generated based on a user's input. For example, the parameter(s) of a dose estimation model may be selected or entered via a graphical user interface (GUI) provided by a computer system implementing a knowledge-based planning system, etc. The specific parameter(s) may depend on the clinician's experience and knowledge, type of radiotherapy treatment required, beam configuration (e.g., energy, collimator size and orientations), etc. The clinician may also rely on any expertise or knowledge relating to the biological effect of radiation on target 146 and/or OAR 148, such as based on tumor control probability, normal tissue complication probability, etc. The tumor control probability is the probability of eradicating all tumor cells as a function of dose. The normal tissue complication probability is the probability of, as a function of dose, inducing some particular complication (a collective word for describing a variety of conditions such as nausea, vomiting, etc.) in a normal organ. Multiple targets and OARs of any suitable shapes and sizes may be modeled.

At 320 in FIG. 3 (related to 220 in FIG. 2), training data that includes N treatment plans (see 325) associated with respective multiple past patients is obtained, such as by retrieving from a database of past treatment plans (see 315), receiving from another computer system via a communication link, etc. Training data 325 may be obtained based on their relevance to a particular treatment site, such as the prostate region in the example in FIG. 3. A search may be performed based on any suitable search criteria, such as target name, treatment site, dose prescription level, patient's data (e.g., gender, age), diagnostic data (if available), existing contours, etc. A particular treatment plan in training data 320 may be denoted as the $i^{th}$ treatment plan, where i=1, . . . , N.

At 330 in FIG. 3, training data 325 may be processed to extract various data required to train or generate the dose estimation model (as defined by model configuration data 310). Here, the term "process" or "processing" may include any suitable data processing operation(s), such as data analysis, feature extraction, calculation, derivation, transformation, any combination thereof, etc. In particular, the $i^{th}$ treatment plan may be processed to determine $(X_i, Y_i)$, where $X_i$=structure data identifying K≥1 anatomical structure parameter(s), $Y_i$=dose data identifying L≥1 dose parameter(s) and i=1, . . . , N.

In practice, $X_i=(X_{i1}, \ldots, X_{iK})$ represents the "independent" parameter(s) of the dose estimation model. For example, $X_i$ may include any suitable structure parameter(s) that can be extracted or derived from the $i^{th}$ treatment plan, such as target volume, OAR volume, relative overlap volume (i.e., fraction of target volume overlapping with OAR volume), relative out-of-field volume (i.e., fraction of target or OAR volume outside of the treatment field), distance-to-target histogram (DTH) values, any combination thereof, etc. DTH values measure the distance of a particular structure (e.g., OAR) from a particular target.

Further, $Y_i=(Y_1, \ldots, Y_{iL})$ represents the "dependent" parameter(s) of the dose estimation model. For example, $Y_i$ may include any suitable dose parameter(s) that can be extracted or derived from the $i^{th}$ treatment plan, such as mean dose, median dose, 3D dose distribution, dose-volume histograms (DVH), etc. In general, a 3D dose distribution defines the magnitude of radiation at each voxel representing a target or OAR. 3D dose distributions may be summarized using DVH in a 2D format. Radiation dose may be measured in Gray (Gy), which represents the absorption of one joule of radiation energy in one kilogram of matter.

For simplicity, consider an example with K=4 and L=1 for prostate cancer treatment planning in FIG. 3. In this case, $Y_i$ is a 1D vector with a singular value $Y_i$. Accordingly, structure data and dose data from the $i^{th}$ treatment plan may be expressed as $(X_i, Y_i)=X_{i1}, X_{i2}, X_{i3}, X_{i4}, Y_i)$, where $X_{i1}$=prostate volume; $X_{i2}$=rectum volume; $X_{i3}$=bladder volume; $X_{i4}$=femoral head volume; and $Y_i$=mean radiation dose on prostate. It should be understood that any additional and/or alternative parameter(s) may be used in practice.

Automatic Segmentation

At 340 in FIG. 3 (related to 230 in FIG. 2), outlier detection is performed to identify outlier treatment plans 345 ("first treatment plans" in FIG. 2) from training data 325 that includes N treatment plans. At 350 in FIG. 3, other treatment plans may be classified as "non-outlier" treatment plans 355 ("second treatment plans" in FIG. 2). The detection at blocks 340-350 may be based on model configuration data 310, structure data $(X_i)$, dose data $(Y_i)$, or any combination thereof. Any suitable criteria for outlier detection may be used. For example, outlier treatment plan 345 may be a geometric outlier, dosimetric outlier, etc.

In relation to geometric outlier detection, outlier treatment plan 345 may be detected based on model configuration data 310 and structure data $(X_i)$. For example, the $i^{th}$ treatment plan may be a geometric outlier based on a sub-optimal characteristic, such as missing, invalid or unreliable data in structure data $(X_i)$. The missing data may be detected by comparing the structure parameters required by the dose estimation model (as specified by model configuration data 310), and structure data $X_i=(X_{i1}, \ldots, X_{iK})$ extracted from the $i^{th}$ treatment plan. In the example FIG. 3, $X_{i4}$=femoral head volume may be missing (or set to an invalid value) because it is not contoured. In practice, the missing data may be detected by programmatically checking the IDs of segmented structures in each treatment plan. It should be understood that it is not necessary for each and every treatment plan to have all the structures included in the dose estimation model.

In practice, it is useful to detect geometric outliers (e.g., unreliable treatment plans) because they might tilt the resulting dose estimation model more strongly towards a less accurate estimation compared to non-outliers. For example, geometric outlier detection 340 may involve assessing the reliability of structure data $(X_i)$ using a computer system, such as by comparing the size (or shape) of an organ with a distribution of organ sizes (or shapes) already present in the model. In general, the geometric outliers may be at odds with the statistics of the non-outliers. Some example ways to assess the reliability of structure data $(X_i)$ are as follows. For example, a bladder volume may be unreliable when it is significantly larger than the ninth percentile of the distribution of known bladder volumes. In other examples, a dice score between (manually drawn) organ and its auto-segmented counterpart may be exceptionally low, or volumes of the left and right lungs may differ more than expected. For parameters related to a structure's location, geometric outlier detection 340 may involve estimating how much the organ is in-field, or overlapping with a target. Any alternative and/or additional approaches may be used.

In relation to dosimetric outlier detection, outlier treatment plan 345 may be detected based on dose data $(Y_i)$. For example, the $i^{th}$ treatment plan may be a dosimetric outlier based on a sub-optimal characteristic, such as its dose data not satisfying certain thresholds, following a dose distribution, etc. In practice, the sub-optimal characteristic in dose data $(Y_i)$ may be caused by missing, invalid or unreliable data in structure data $(X_i)$. For example, a treatment plan for a head and neck patient may have abnormally low dose for the right parotid due to missing contours for the left parotid. Here, the term "abnormal" may be based on a regression model built using data from other patients with missing data for the left parotid. The low dose for the right parotid may be caused by the left parotid being sacrificed as a planning trade-off (which also could be the reason why it is not contoured).

At 360 in FIG. 3 (related to 240 in FIG. 2), in response to detecting outlier treatment plan 345, automatic segmentation is performed to generate improved treatment plan 365 with updated structure data ($X_i$). In the example in FIG. 3, automatic segmentation may be performed to segment or contour anatomical structure(s) that are missing from structure data ($X_i$), or re-segment existing anatomical structure(s) that appear invalid or unreliable. Updated structure data ($X_i$) may be stored with the original treatment plan 345 in database 315 or saved as part of the model binary of dose estimation model 375.

An automatic segmentation engine may be configured to perform segmentation at block 360 for a single structure, or multiple structures. For example, if outlier treatment plan 345 only has bladder, rectum and prostate contoured, the automatic segmentation engine that provides femoral head contours may be used. This might be a separate model just for that one structure or the femoral heads might be one of the outputs of a multi-organ model. Any suitable automatic segmentation approach may be implemented, such as deep learning engines (e.g., deep neural networks), machine learning algorithms, and non-learning algorithms. In the following, some examples will be discussed using FIG. 4A and FIG. 4B.

(a) Deep Learning Engine

Figure 4A:
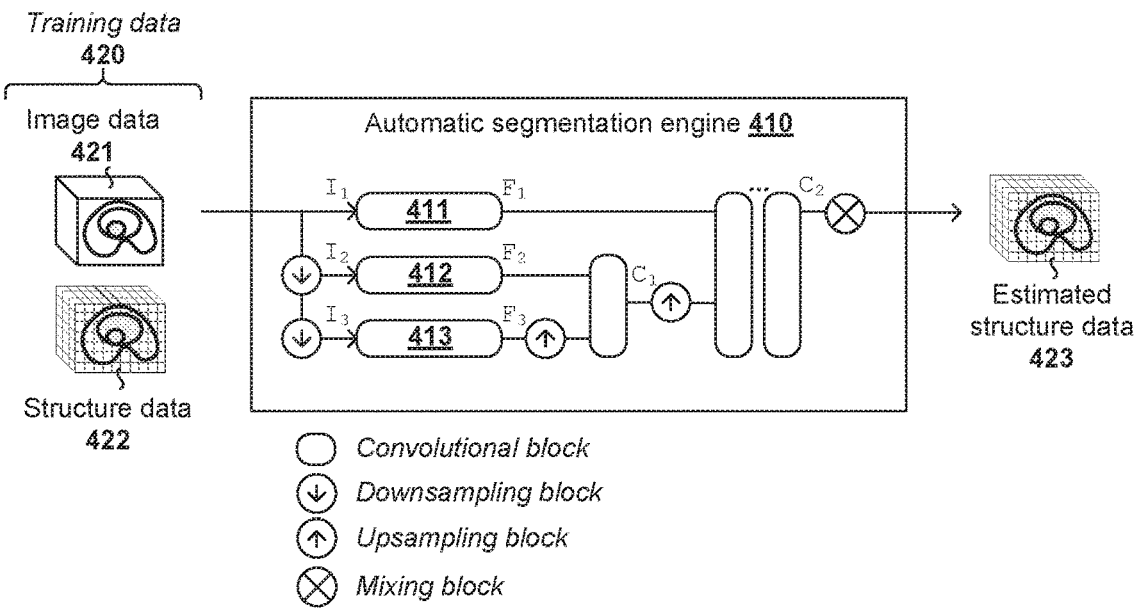
FIG. 4A is a schematic diagram illustrating a first example automatic segmentation engine for radiotherapy treatment planning.
Figure 4A:
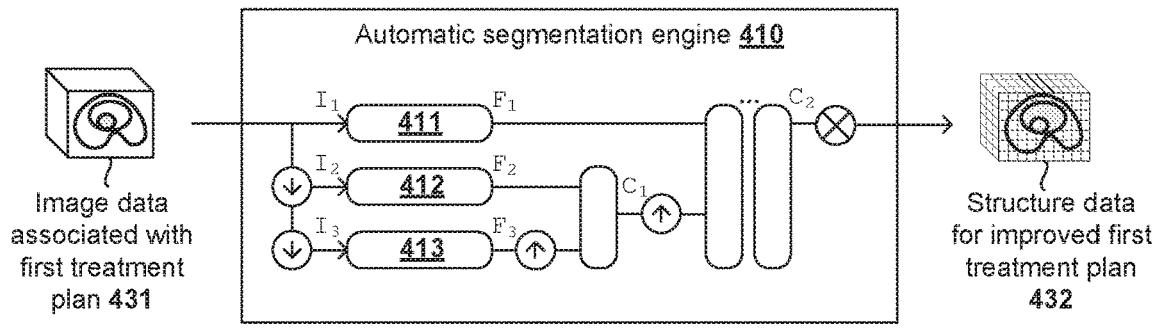

FIG. 4A is a schematic diagram illustrating first example automatic segmentation engine 410 for radiotherapy treatment planning. Throughout the present disclosure, the term "deep learning" may refer generally to a class of approaches that utilizes many layers or stages of nonlinear data processing for feature learning as well as pattern analysis and/or classification. Accordingly, the term "deep learning model" may refer to a hierarchy of "layers" of nonlinear data processing that include an input layer, an output layer, and multiple (i.e., two or more) "hidden" layers between the input and output layers. These layers may be trained from end-to-end (e.g., from the input layer to the output layer) to extract feature(s) from an input and classify the feature(s) to produce an output (e.g., classification label or class). The term "deep learning engine" may refer to any suitable hardware and/or software component(s) of a computer system that are capable of executing algorithms according to any suitable deep learning model(s).

Depending on the desired implementation, any suitable deep learning model(s) may be used, such as convolutional neural network, recurrent neural network, deep belief network, or any combination thereof, etc. In practice, a neural network is generally formed using a network of processing elements (called "neurons," "nodes," etc.) that are interconnected via connections (called "synapses," "weights," etc.). For example, convolutional neural networks may be implemented using any suitable architecture(s), such as U-net, LeNet, AlexNet, ResNet, V-net, DenseNet, etc. In this case, a "layer" of a convolutional neural network may be a convolutional layer, pooling layer, rectified linear units (ReLU) layer, fully connected layer, loss layer, etc. In practice, the U-net architecture includes a contracting path (left side) and an expansive path (right side). The contracting path includes repeated application of convolutions, followed by a ReLU layer and max pooling layer. Each step in the expansive path may include upsampling of the feature map followed by convolutions, etc.

During training phase 401, deep learning engine 410 may be trained using any suitable training data 421-422 relating to automatic segmentation. In practice, training data 421-422 may include example input data=unsegmented image data 421, and example output data=structure data 422 (also known as segmentation data). Structure data 422 may identify any suitable contour, shape, size and/or location of structure(s) or segment(s) of a patient's anatomy, such as target(s), OAR(s), etc. Image data 421 may include 2D or 3D images of the patient's anatomy, and captured using any suitable imaging modality or modalities.

The aim of training phase 401 is to train deep learning engine 410 to perform automatic segmentation by mapping input data=image data 421 to example output data=structure data 422. Training phase 401 may involve finding weights that minimize the training error between training structure data 422, and estimated structure data 423 generated by deep learning engine 410. For example, in relation to prostate cancer, image data 421 may include image data of a patient's prostate region. In this case, structure data 422 may identify anatomical structures in the prostate region, such as the patient's prostate, rectum, bladder and femoral heads. In practice, deep learning engine 410 may be trained identify a particular structure (i.e., single-structure model), or multiple structures (i.e., multi-structure model to identify targets and OARs of any suitable shapes and sizes).

Once trained, deep learning engine 410 may be used to perform automatic segmentation at block 360 in FIG. 3 during inference phase 402. In particular, based on image data 431 associated with outlier treatment plan 345, automatic segmentation may be performed to generate improved structure data 432. In the case of missing data, improved structure data 432 may identify additional anatomical structure(s), such as $X_{i4}$=femoral head volume missing from outlier treatment plan 345. In the case of invalid or unreliable data, improved structure data 432 associated with existing anatomical structure(s) may be generated, such as by re-contouring the structures, etc. A size check may be performed to determine whether the volume of a contoured structure (e.g., OARs) falls within the distribution of sizes already in the model. This may involve comparing the size of the contoured structure with the mean size in the model, such as whether it is within two to three standard deviations.

Depending on the desired implementation, deep learning engine 410 may include multiple processing pathways 411-413 described in related U.S. patent application Ser. No. 16/145,461. In the example in FIG. 4A, three processing pathways 411-413 (k=1, 2, 3) to process image data at different resolution levels ($R_k$=$R_1$, $R_2$, $R_3$). First processing pathway 411 (k=1) is configured to process input=first image data ($I_1$) at a first resolution level $R_1$ (e.g., 1×). Second processing pathway 412 (k=2) is configured to process input=second image data ($I_2$) at a second resolution level $R_2 < R_1$ to enlarge the receptive field. Third processing pathway 413 (k=3) is configured to process input=third image data ($I_3$) at a third resolution level $R_3 < R_2 < R_1$ to further enlarge the receptive field.

The outputs of processing pathway 411-413 are first feature data ($F_1$), second feature data ($F_2$) and third feature data ($F_3$), respectively. Third feature data ($F_3$) may be upsampled using an upsampling block (e.g., by a factor of 4×) before being combined with second feature data ($F_2$) using a convolutional block, thereby generating first combined set ($C_1$). Further, first combined set ($C_1$) may be upsampled using upsampling blocks (e.g., by a factor of 2×) before being combined with first feature data ($F_1$) using convolutional blocks, thereby generating second combined set ($C_2$). Mixing block(s) may be configured to massage (e.g., using 1×1×1 convolutions) the final set of features into the final result.

By processing image data 421/431 at multiple resolution levels, processing pathways 411-413 provide different views into image data 421/431 to achieve a larger receptive field. In practice, medical image data generally includes both local and global feature data of a patient's anatomy, where the terms "local" and "global" are relative in nature. For example, the local feature data may provide a microscopic view of the patient's anatomy, such as tissue texture, whether a structure has a limiting border, etc. In contrast, the global feature data may provide a relatively macroscopic view of the patient's anatomy, such as which region the anatomy is located (e.g., prostate, etc.), orientation (e.g., to the left, to the right, front, back), etc. Any alternative and/or additional model(s) may be used by deep learning engine 410.

(b) Machine Learning and Other Algorithms

Figure 4B:
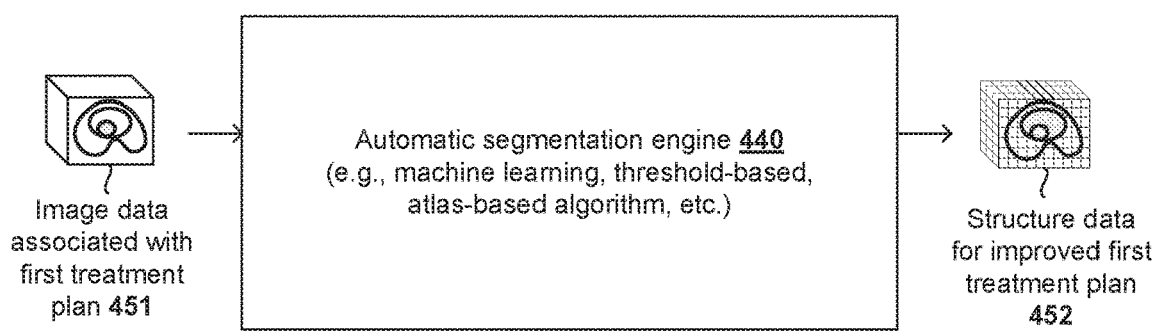
FIG. 4B is a schematic diagram illustrating a second example automatic segmentation engine for radiotherapy treatment planning.

FIG. 4B is a schematic diagram illustrating second example automatic segmentation engine 440 for radiotherapy treatment planning. Similar to the example in FIG. 4A, automatic segmentation engine 440 is configured to perform automatic segmentation on image data 451 associated with outlier treatment plan 345 to generate improved structure data 452. In one example, automatic segmentation engine 440 may implement a machine learning algorithm, such as support vector machine, k-nearest neighbors, etc. In another example, automatic segmentation engine 440 may implement a non-learning algorithm, such as a threshold-based algorithm that performs thresholding to certain Hounsfield number (HU) values, atlas-based algorithm, etc. The atlas-based algorithm maps current patient geometry to some pre-contoured patient geometry and then defines the structures into the current patient geometry using a deformation field between the two patient geometries.

Dose Estimation Model Generation

Referring now to 370 in FIG. 3 (related to 250 in FIG. 2), dose estimation model 375 is trained using improved training data that includes improved treatment plans 365 (generated from outlier treatment plans 345), and non-outlier treatment plans 355. Dose estimation model 375 is trained to estimate a relationship that transforms independent structure data (X) to dependent dose data (Y). For example, the relationship or interdependency may be expressed using any suitable function $f( )$ for $Y=f(X)$.

Any suitable algorithm may be used to estimate function $f( )$ such as regression algorithm (e.g., stepwise multiple regression, linear regression, polynomial regression, etc.) to estimate a set of coefficients that transform X to Y. It should be understood that any additional and/or alternative algorithm may be used to train the dose estimation model, such as principal component analysis (PCA) algorithm, classification algorithm, clustering algorithm, machine learning algorithm, etc. Function $f( )$ may be presented as a multiplication of X with a matrix of coefficients. For example, assuming $f( )$ is linear, linear regression may be used to estimate the following dose estimation model:

$$Y_i = \alpha + \beta_1 X_{i1} + \beta_2 X_{i2} + \beta_3 X_{i3} + \beta_4 X_{i4} + \varepsilon_1.$$

In the above equation, $\beta_1$, $\beta_2$, $\beta_3$ and $\beta_4$ are known as the coefficients associated with respective independent features $X_{i1}$, $X_{i2}$, $X_{i3}$, $X_{i4}$ and $Y_i$; and $\alpha$ is also known as the intercept. In general, the coefficients may be dimensionless. To estimate $f( )$ values of the coefficients that best fit training data 320 are calculated, such as by minimizing the least-squared errors $\varepsilon^2 = (f(X) - Y)^2$.

As shown at 380 in FIG. 3, an iterative process may be performed to generate dose estimation model 375. For example, once dose estimation model 375 is generated, further improvements may be made by performing automatic segmentation to further improve the training data, and so on. In practice, a few iterations may be required. In the first iteration, for example, there is no dose estimation model 375 available, in which case it may be difficult to use dosimetric information to determine outliers. Since the model changes at each iteration, more than two iterations may be performed. The stopping criterion for the iterative process may be the detection of two consecutive iterations that lead to the same result in the outlier analysis at block 340. Alternatively and/or additionally, it would be practical to limit the number of iterations by setting a maximum iteration count to be the stopping criterion.

Depending on the desired implementation, the iterative process at 380 may involve iterating over different treatment plans, such as when new treatment plans (i.e., training data) are available in database 315. In this case, automatic segmentation that is performed on new treatment plans (or outliers among them) may result in the changes of volumetric parameters. This way, treatment plans may be used to improve dose estimation model 375 over time.

In practice, automatic segmentation may be implemented to reduce or ameliorate the above issues to achieve a more consistent segmentation result across the training dataset. This way, all treatment plans associated with dose estimation model 375 would have all the anatomical structures used in the model. Conventionally, this is not the case, and some structures might be modeled in a sub-optimal manner. In this case, the resulting dose estimation model may not be meaningful because there is insufficient data for a proper regression model.

Additionally, when a new treatment plan is added to dose estimation model 375, automatic segmentation may be performed on the image data associated with the new treatment plan to contour all the anatomical structures required by dose estimation model 375 automatically. By checking the difference between original and automatically segmented organs, one could even identify potentially incorrectly contoured original structures or wrongly matched structures. Some measures of difference from automatically contoured structure could even be an independent parameter in the model (used either in the prediction or when the accuracy of the prediction is estimated). For example, in the DVH estimation of dose estimation model 375, the regression model may utilize the OAR absolute volume. In a more general case, a deep neural network solution of dose estimation may be affected by any shape change in the organ. As such, any measure of difference may contribute to the dose estimation.

Dose Estimation and Treatment Delivery

Figure 5:
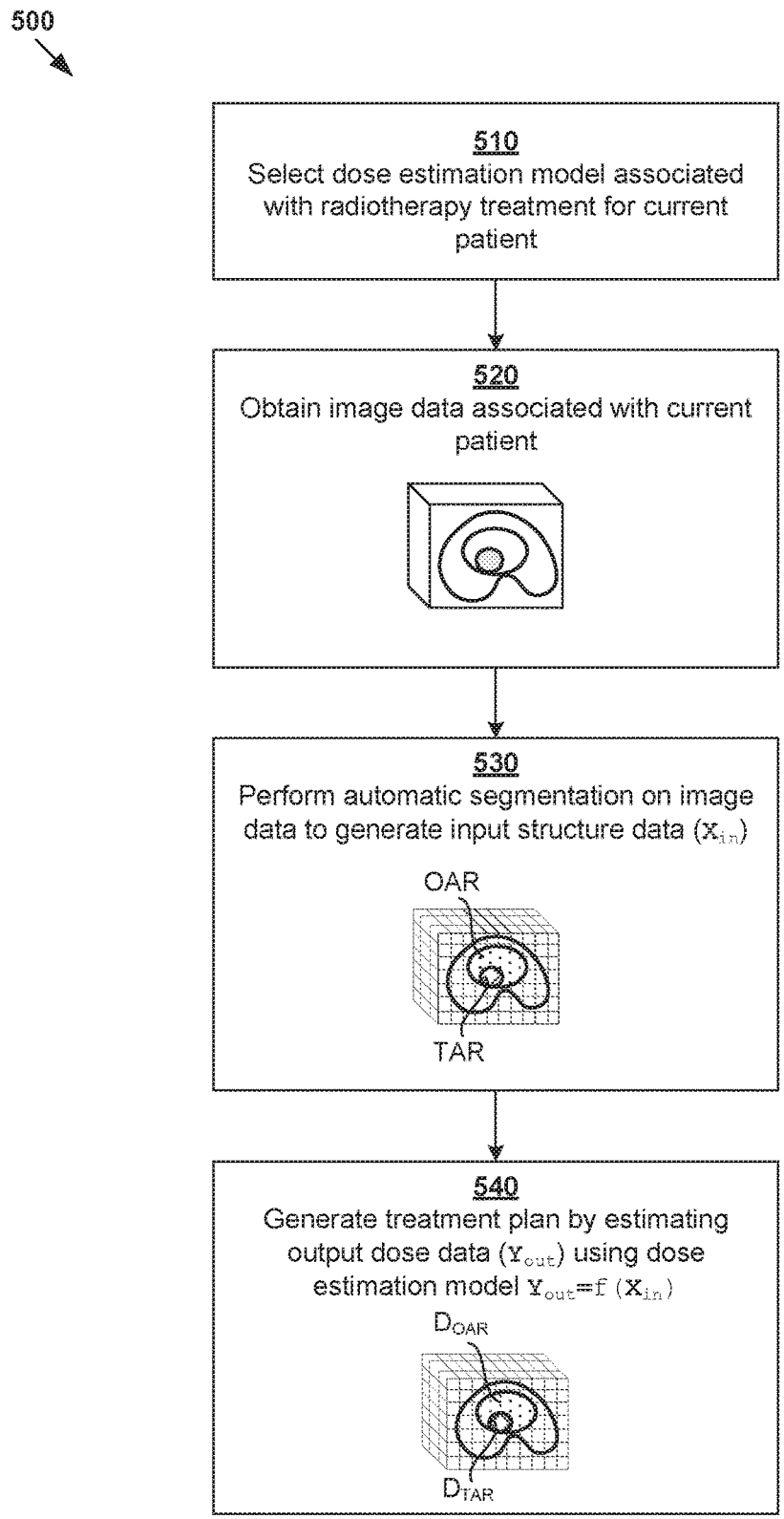
FIG. 5 is a flowchart of an example process for a computer system to generate dose data using a dose estimation model.

FIG. 5 is a flowchart of example process 500 for a computer system to generate dose data using dose estimation model 375. The various blocks may be combined into fewer blocks, divided into additional blocks, and/or eliminated based upon the desired implementation. Similar to the example in FIG. 2, example process 500 may be implemented using any suitable computer system, an example of which will be discussed using FIG. 7.

At 510 in FIG. 5, a dose estimation model is selected for the radiotherapy treatment planning of a particular current patient. In practice, example process 300 in FIG. 3 may be repeated to determine multiple dose estimation models from a single set of training data, or multiple sets. The dose estimation model may be selected based on any suitable factor(s), such as a treatment region of the patient, etc.

At 520 and 530 in FIG. 5, image data associated with the current patient is obtained, and automatic segmentation performed to generate input structure data ($X_{in}$) based on the image data. The image data may be "obtained" using any suitable approach, such as received via a GUI provided by the computer system, retrieved from storage, etc. At 540 in FIG. 5, based on structure data ($X_{in}$), output dose data ($Y_{out}$) may be estimated using dose estimation model 375 in FIG. 3.

Using the prostate cancer example in FIG. 3 again, input structure data ($X_{in}$) generated using automatic segmentation may include $X_1$=prostate volume; $X_2$=rectum volume; $X_3$=bladder volume and $X_4$=femoral head volume. In this case, output dose data ($Y_{out}$) estimated using dose estimation model 375 may include $Y_i$=mean radiation dose on prostate. In practice, estimates produced by dose estimation model 375 may be optimized according to other objectives set by the clinician to produce complete treatment plan.

Figure 6:
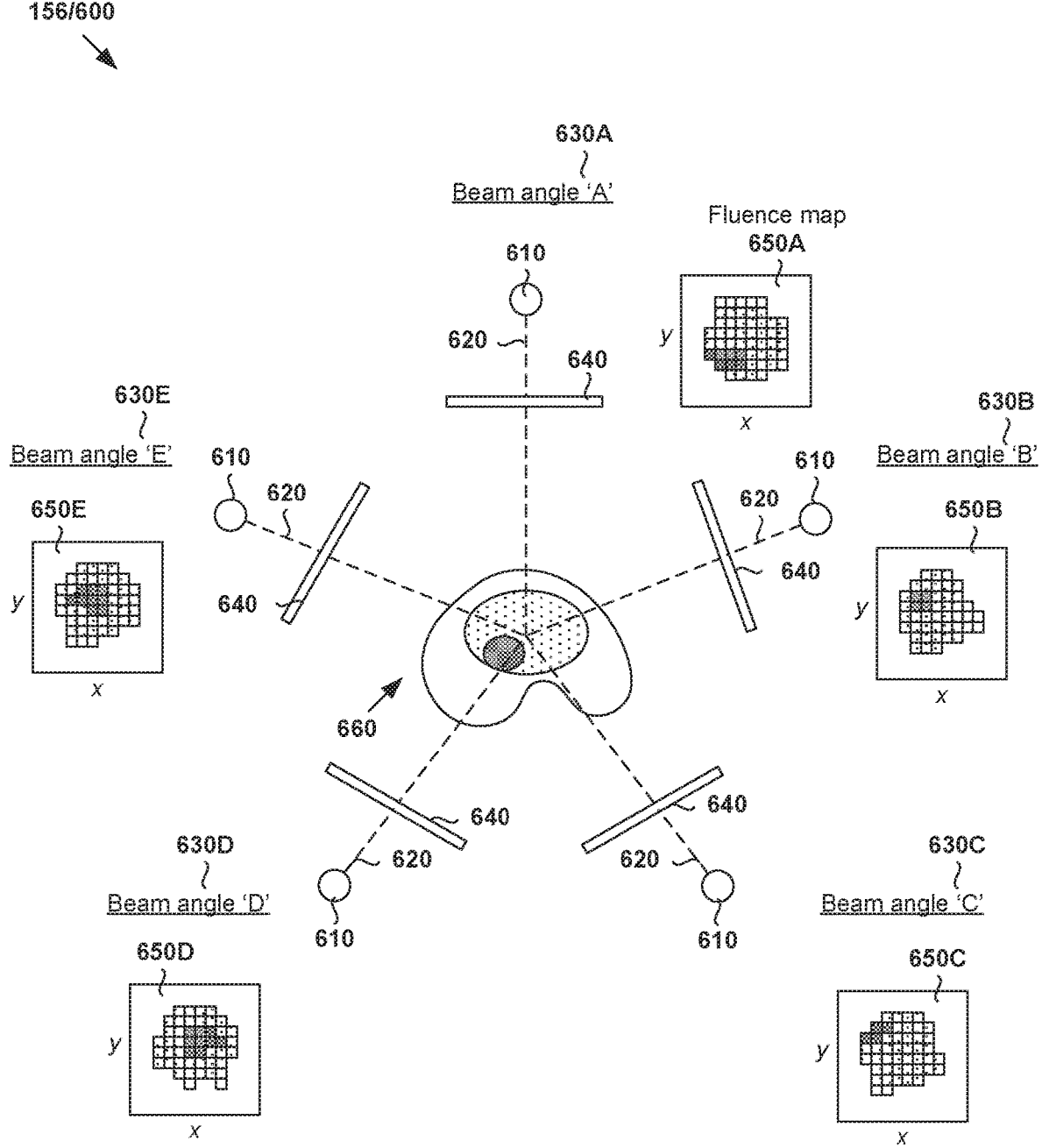
FIG. 6 is a schematic diagram of an example radiotherapy treatment system for treatment delivery according to dose data generated according to the example in FIG. 5.

A treatment plan is generated based on output dose data ($Y_{out}$) for treatment delivery. FIG. 6 is a schematic diagram illustrating example radiotherapy treatment system 600 for treatment delivery according to dose data generated according to the example in FIG. 5. Although an example is shown in FIG. 6, it will be appreciated any alternative and/or additional configuration may be used depending on the desired implementation. Radiotherapy treatment system 600 includes radiation source 610 to project radiation beam 620 onto a treatment volume representing the patient's anatomy at various beam angles 630.

In practice, radiation source 610 may include a linear accelerator to accelerate radiation beam 620 and a collimator (e.g., MLC) to modify or modulate radiation beam 620. In another example, radiation beam 620 may be modulated by scanning it across a target patient in a specific pattern with various energies and dwell times (e.g., as in proton therapy). A controller (e.g., computer system) may be used to control the operation of radiation source 620 according to treatment plan 156.

During treatment delivery, radiation source 610 may be rotatable using a gantry around a patient, or the patient may be rotated (as in some proton radiotherapy solutions) to emit radiation beam 620 at various beam orientations or angles relative to the patient. For example, five equally-spaced beam angles 630A-E (also labelled "A," "B," "C," "D" and "E") may be selected using a deep learning engine configured to perform treatment delivery data estimation. In practice, any suitable number of beam and/or table or chair angles 630 (e.g., five, seven, etc.) may be selected. At each beam angle, radiation beam 620 is associated with fluence plane 640 (also known as an intersection plane) situated outside the patient envelope along a beam axis extending from radiation source 610 to treatment volume 660. As shown in FIG. 6, fluence plane 640 is generally at a known distance from the isocenter.

Computer System

Figure 7:
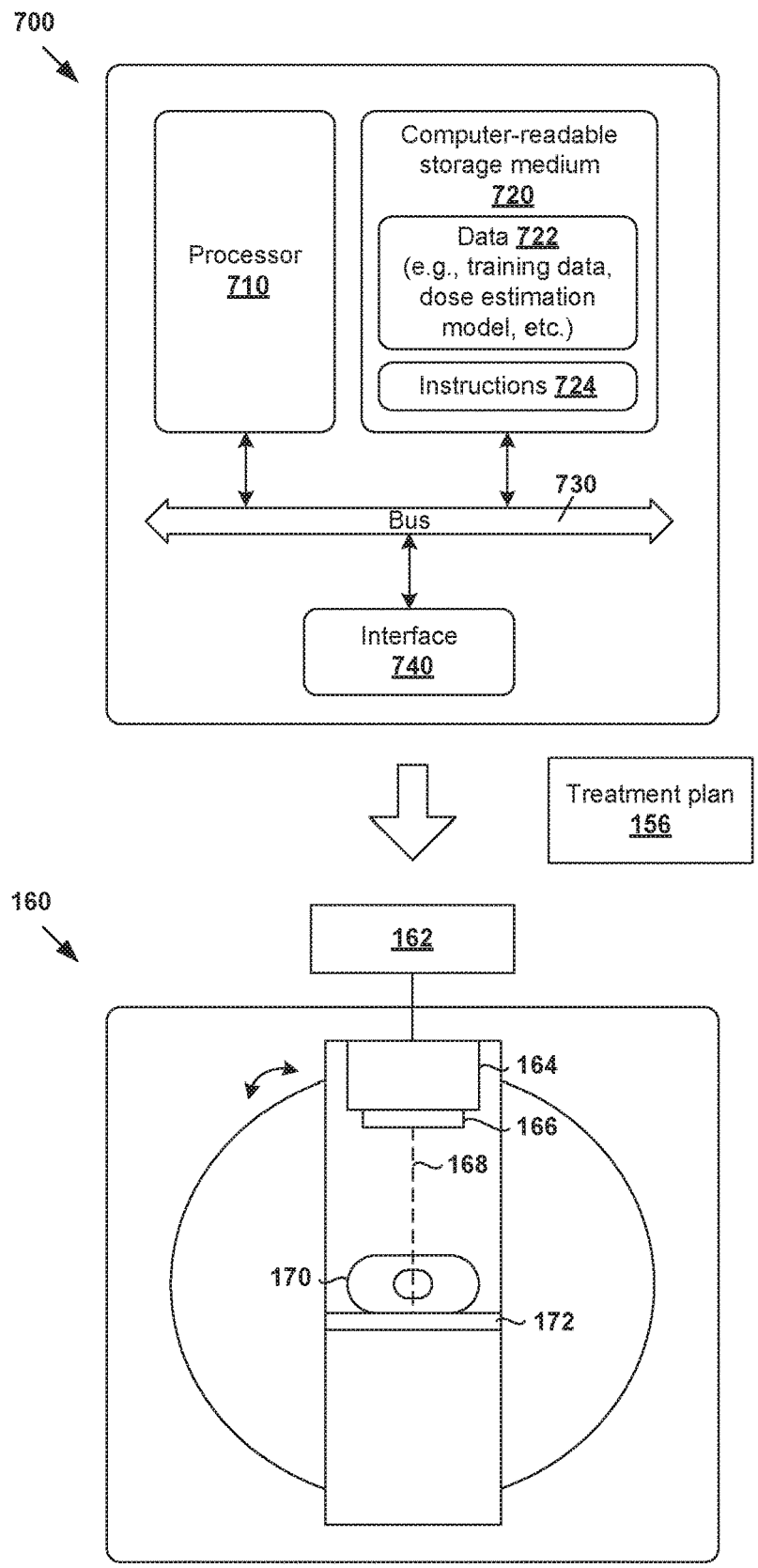
FIG. 7 is a schematic diagram of an example computer system to generate a dose estimation model for radiotherapy treatment planning and an example radiotherapy treatment system for treatment delivery.

The above examples can be implemented by hardware, software or firmware or a combination thereof. FIG. 7 is a schematic diagram of example computer system 700 for radiotherapy treatment planning. In this example, computer system 705 (also known as a treatment planning system) may include processor 710, computer-readable storage medium 720, interface 740 to interface with radiotherapy treatment delivery system 160, and bus 730 that facilitates communication among these illustrated components and other components.

Processor 710 is to perform processes described herein with reference to FIG. 1 to FIG. 6. Computer-readable storage medium 720 may store any suitable information 722, such as information relating to training data, dose estimation models, deep learning engines, input data, output data, etc. Computer-readable storage medium 720 may further store computer-readable instructions 724 which, in response to execution by processor 710, cause processor 710 to perform processes described herein. Treatment may be delivered according to treatment plan 156 using treatment planning system 160 explained using FIG. 1, the description of which will not be repeated here for brevity.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. Throughout the present disclosure, the terms "first," "second," "third," etc. do not denote any order of importance, but are rather used to distinguish one element from another.

Those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure.

Although the present disclosure has been described with reference to specific exemplary embodiments, it will be recognized that the disclosure is not limited to the embodiments described, but can be practiced with modification and alteration within the spirit and scope of the appended claims. Accordingly, the specification and drawings are to be regarded in an illustrative sense rather than a restrictive sense.

We claim:

1. A method for a computer system to generate a dose estimation model for radiotherapy treatment planning, wherein the method comprises:
    obtaining model configuration data associated with the dose estimation model, wherein the model configuration data specifies multiple anatomical structures based on which dose estimation is performed by the dose estimation model;
    obtaining training data that includes a first treatment plan associated with a first past patient and multiple second treatment plans associated with respective multiple second past patients;
    determining that automatic segmentation is required for the first treatment plan, and in response to said determining,
        performing automatic segmentation on image data associated with the first past patient to generate an improved first treatment plan that includes structure data identifying at least one of the multiple anatomical structures; and generating the dose estimation model based on the improved first treatment plan and the multiple second treatment plans.

2. The method of claim 1, wherein determining that automatic segmentation is required comprises:
   processing the first treatment plan to extract first structure data and first dose data associated with the first past patient; and
   determining whether the first treatment plan is an outlier based on at least one of the following: the model configuration data, the first structure data and the first dose data.

3. The method of claim 2, wherein determining that automatic segmentation is required comprises:
   determining the first treatment plan to be a geometric outlier based on a sub-optimal characteristic associated with the first structure data.

4. The method of claim 3, wherein determining that automatic segmentation is required comprises:
   comparing the first structure data with the model configuration data to identify the sub-optimal characteristic in the form of missing data in the first structure data.

5. The method of claim 2, wherein determining that automatic segmentation is required comprises:
   determining the first treatment plan to be a dosimetric outlier based on a sub-optimal characteristic associated with the first dose data.

6. The method of claim 1, wherein generating the improved first treatment plan comprises:
   performing automatic segmentation on the image data to generate the improved structure data using a deep learning engine.

7. The method of claim 1, wherein generating the improved first treatment plan comprises:
   performing automatic segmentation on the image data to generate the improved structure data using one of the following: a machine learning algorithm, a threshold-based algorithm, and an atlas-based algorithm.

8. A non-transitory computer-readable storage medium that includes a set of instructions which, in response to execution by a processor of a computer system, cause the processor to perform a method of generating a dose estimation model for radiotherapy treatment planning, wherein the method comprises:
   obtaining model configuration data associated with the dose estimation model, wherein the model configuration data specifies multiple anatomical structures based on which dose estimation is performed by the dose estimation model;
   obtaining training data that includes a first treatment plan associated with a first past patient and multiple second treatment plans associated with respective multiple second past patients;
   determining that automatic segmentation is required for the first treatment plan, and in response to said determining,
      performing automatic segmentation on image data associated with the first past patient to generate an improved first treatment plan that includes structure data identifying at least one of the multiple anatomical structures; and
      generating the dose estimation model based on the improved first treatment plan and the multiple second treatment plans.

9. The non-transitory computer-readable storage medium of claim 8, wherein determining that automatic segmentation is required comprises:
   processing the first treatment plan to extract first structure data and first dose data associated with the first past patient; and
   determining whether the first treatment plan is an outlier based on at least one of the following: the model configuration data, the first structure data and the first dose data.

10. The non-transitory computer-readable storage medium of claim 9, wherein determining that automatic segmentation is required comprises:
    determining the first treatment plan to be a geometric outlier based on a sub-optimal characteristic associated with the first structure data.

11. The non-transitory computer-readable storage medium of claim 10, wherein determining that automatic segmentation is required comprises:
    comparing the first structure data with the model configuration data to identify the sub-optimal characteristic in the form of missing data in the first structure data.

12. The non-transitory computer-readable storage medium of claim 9, wherein determining that automatic segmentation is required comprises:
    determining the first treatment plan to be a dosimetric outlier based on a sub-optimal characteristic associated with the first dose data.

13. The non-transitory computer-readable storage medium of claim 8, wherein generating the improved first treatment plan comprises:
    performing automatic segmentation on the image data to generate the improved structure data using a deep learning engine.

14. The non-transitory computer-readable storage medium of claim 8, wherein generating the improved first treatment plan comprises:
    performing automatic segmentation on the image data to generate the improved structure data using one of the following: a machine learning algorithm, a threshold-based algorithm, and an atlas-based algorithm.

15. A computer system configured to generate a dose estimation model for radiotherapy treatment planning, the computer system comprising: a processor and a non-transitory computer-readable medium having stored thereon instructions that, when executed by the processor, cause the processor to:
    obtain model configuration data associated with the dose estimation model, wherein the model configuration data specifies multiple anatomical structures based on which dose estimation is performed by the dose estimation model;
    obtain training data that includes a first treatment plan associated with a first past patient and multiple second treatment plans associated with respective second past patients;
    determine that automatic segmentation is required for the first treatment plan, and in response to said determining,
       perform automatic segmentation on image data associated with the first past patient to generate an improved first treatment plan that includes structure data identifying at least one of the multiple anatomical structures; and
       generate the dose estimation model based on the improved first treatment plan and the multiple second treatment plans.

16. The computer system of claim 15, wherein the instructions for determining that automatic segmentation is required cause the processor to:

process the first treatment plan to extract first structure data and first dose data associated with the first past patient; and determine whether the first treatment plan is an outlier based on at least one of the following: the model configuration data, the first structure data and the first dose data.

17. The computer system of claim 16, wherein the instructions for determining that automatic segmentation is required cause the processor to:

determine the first treatment plan to be a geometric outlier based on a sub-optimal characteristic associated with the first structure data.

18. The computer system of claim 17, wherein the instructions for determining that automatic segmentation is required cause the processor to:

compare the first structure data with the model configuration data to identify the sub-optimal characteristic in the form of missing data in the first structure data.

19. The computer system of claim 16, wherein the instructions for determining that automatic segmentation is required cause the processor to:

determine the first treatment plan to be a dosimetric outlier based on a sub-optimal characteristic associated with the first dose data.

20. The computer system of claim 15, wherein the instructions for generating the improved first treatment plan cause the processor to:

perform automatic segmentation on the image data to generate the improved structure data using a deep learning engine.

21. The computer system of claim 15, wherein the instructions for generating the improved first treatment plan cause the processor to:

perform automatic segmentation on the image data to generate the improved structure data using one of the following: a machine learning algorithm, a threshold-based algorithm, and an atlas-based algorithm.

* * * * *